United States Patent [19]

Allan

[11] 4,438,137
[45] Mar. 20, 1984

[54] PESTICIDAL COMPOSITIONS EMPLOYING AMITRAZ WITH STABILIZER

[75] Inventor: Keith Allan, Loughborough, England

[73] Assignee: FBC Limited, Hauxton, England

[21] Appl. No.: 393,277

[22] Filed: Jun. 29, 1982

Related U.S. Application Data

[63] Continuation-in-part of Ser. No. 179,588, Aug. 21, 1980, abandoned.

[30] Foreign Application Priority Data

Sep. 20, 1979 [GB] United Kingdom ................ 7932636

[51] Int. Cl.$^3$ ............................................ A01N 33/02
[52] U.S. Cl. ..................................... 424/330; 424/225
[58] Field of Search ................................ 424/325, 330

[56] References Cited

U.S. PATENT DOCUMENTS 3,175,896 3/1965 Arndet et al. .......................... 71/2.3

FOREIGN PATENT DOCUMENTS 1327935 8/1973 United Kingdom .
1519728 8/1978 United Kingdom .

*Primary Examiner*—Allen J. Robinson
*Attorney, Agent, or Firm*—Lawrence Rosen

[57] ABSTRACT

A liquid pesticidal composition contains the pesticide amitraz and di-(2,6-di-isopropylphenyl) carbodiimide or dicyclohexylcarbodiimide. The carbodiimide acts as a stabilizer for the composition to prevent degradation of the amitraz.

6 Claims, No Drawings

PESTICIDAL COMPOSITIONS EMPLOYING AMITRAZ WITH STABILIZER

This application is a continuation-in-part of application Ser. No. 179,588, filed Aug. 21, 1980, now abandoned.

BACKGROUND OF THE INVENTION

This invention relates to pesticidal compositions and in particular to compositions containing the pesticidal compound, amitraz.

Amitraz has the chemical formula 1,5-di-(2,4-dimethylphenyl)-3-methyl-1,3,5-triazapenta-1,4-diene and has a wide range of insecticidal and acaricidal properties as described in British Patent Specification No. 1,327,935.

SUMMARY OF INVENTION

The present invention provides a liquid insecticidal and acaricidal composition comprising a solution of from about 0.5 to 35% w/v 1,5-di-(2,4-dimethylphenyl)-3-methyl-1,3,5-triazapenta-1,4-diene and from about 0.5 to 5% w/v of a carbodiimide selected from the group consisting of dicyclohexycarbodiimide and di-(2,6-diisopropyl-phenyl) carbodiimide.

All percentage compositions given in this specification are expressed as weight/volume percentages that is the weight of material in grams per 100 milliliters of solution.

The carbodiimide acts as a stabiliser for the compositions of the present invention and may be present in an amount from 0.5 to 5%, preferably 1 to 3%.

In British Pat. No. 1,519,729 certain diphenylcarbodiimides including di-(2,6-diisopropylphenyl) carbodiimide are disclosed as ectoparasiticides. However at the concentration it is incorporated in the amitraz composition it has been found to have substantially no effect on adult spider mites at the rates at which amitraz is normally used.

One form of composition containing amitraz which is supplied for use on both plants and animals is an emulsifiable concentrate which is mixed with water for form an emulsion which may be used as a pesticidal spray, dip or "pour-on" preparation for animals or a pesticidal spray for crops. An emulsifiable concentrate comprises a solution of the active ingredients along with one or more emulsifying agents in a suitable solvent e.g. a water-immiscible solvent.

The emulsifiable concentrate comprises a solution of the active ingredient along with one or more emulsifying agents in a suitable solvent, e.g. a water-immiscible solvent.

The emulsifying agents employed in an emulsifiable concentrate composition may be any of those commonly used in the art and are preferably nonionic surfactants, anionic surfactants or a blend of nonionic and anionic surfactants. The amount of emulsifier present may be up to 30% of the total composition.

Nonionic compounds include for example, ethoxylated alkylphenols such as nonyphenol ethoxylates; ethoxylated aliphatic alcohols; ethoxylated amines; ethoxylated esters; ethoxylated alkylolamides; block polymers/copolymers of ethylene oxide and propylene oxide; or alkylolamides. One material which has been found to be particularly advantageous is an ethoxylated nonylphenol with an ethoxy content of 9.5 moles per mole.

Anionic compounds include for exampoe, sulphonates such as alkylaryl sulphonates or petroleum sulphonates; sulphates such as alcohol sulphates or ether sulphates; phosphate esters; or sulphosuccinates.

The compounds of an emulsifiable concentrate are dissolved in a water-immiscible solvent. Suitable solvents include for example, aromatic hydrocarbons such as alkylbenzenes incorporating the various trimethylbenzenes, methylethylbenzenes, dimethylethylbenzenes, diethylbenzenes, tetramethylbenzenes, trimethylbenzenes, methyldiethylbenzenes, pentamethylbenzenes, naphthalene and various methylnaphthalenes and mixtures thereof; chlorinated hydrocarbons such as chlorinated alkanes, chlorinated alkenes and chlorinated benzene and chlorinated alkylbenzenes; ketonic solvents such as cyclohexanone, isophorone, N-methyl-pyrrolidone, di-isobutylketone and methylisobutylketone.

In addition to emulsifiable concentrates other liquid compositions containing amitraz may be stabilized by the inclusion of carbodiimides. For example, a ULV (ultra-low volume) formulation comprising a solution of amitraz and the carbodiimide in a suitable solvent may be prepared for direct spraying without dilution or a pour-on formulation may be prepared for the direct application to animals by dissolving amitraz and the carbodiimide in an oil medium which may optionally contain a co-solvent.

Other components which may be included in the emulsifiable concentrates of the present invention include additional pesticides.

DESCRIPTION OF PREFERRED EMBODIMENTS

The invention will be illustrated by the following examples of pesticidal composition which are given by way of example only.

EXAMPLE 1

An emulsifiable concentrate was prepared by dissolving amitraz (500 g), di-(2,6-diisopropylphenyl)-carbodiimide sold under the trade name Stabaxol 1 by Bayer (120 g) and a nonylohenol ethoxylate having an ethoxy content of 9.5 mole per mole sold under the trade name Ethylan KEO by Diamond Shamrock Europe Limited (800 g) in a solvent comprising naphthalene and substituted naphthalenes sold under the trade name Esso 200. The solution was made up to 4 liters, filtered and dried using molecular sieve. The composition thus comprised 3% w/v di-(2,6-di-isopropylphenyl) carbodiimide.

The solution was split into two parts for stability testing. The first part was stored at a constant temperature of 50° C. The second part was loaded with a 0.2% w/v of water and stored in the same manner as that of the first part. After six months portions were removed from each of the samples and the amitraz concentration in the portions was determined by gas-liquid chromatography (glc). Within the limits of experimental error no loss of amitraz was observed.

By way of comparison samples of a similar composition but containing no carbodiimide were stored alongside the above samples and were subjected to the same analytical procedures. The samples of concentrate with no added water showed that after 3 months there had been a 3% loss of amitraz and after 6 months a 9% loss of amitraz. In the samples with 0.2% added water the loss of amitraz as 10% after 3 months and 25% after 6 months.

From these results it can be seen that at 50° C. there was a significant loss of amitraz after 6 months storage in concentrates containing no carbodiimide.

EXAMPLE 2

The experiment desribed in Example 1 was repeated with composition containing 1 and 2% of di-(2,6-diisopropylphenyl)-carbodiimide (Stabaxol 1) respectively. The compositions showed no loss of amitraz after 6 months storage at 50° C.

EXAMPLE 3

An emulsifiable concentrate containing amitraz (200 g which is nominally 5.0% w/v) di-(2,6-diisopropylphenyl)-carbodiimide (120 g) and a nonylphenolethoxylate having an ethoxy content of 9.5 mole per mole (Ethylon KEO 800 g) was made up by dissolving the components in an aromatic solvent sold under the trade name Naptha 21/99 by Carless Chemicals Limited, and making the solution up to 4 liters with the solvent. The composition thus comprised 3% w/v di-(2,6-diisopropylphenyl) carbodiimide. The solvent is a 99% aromatic solvent prepared by distilling a heavy naptha $C_9$ feed stock in the range 160° C. to 250° C. The solution was filtered and dried and subjected to stability testing in similar way to that described above for Example 1.

After one years storage at a constant temperature of 50° C., samples containing carbodiimide showed no loss of amitraz within the limits of experimental error whereas similar compositions with no carbodiimide present showed a loss of amitraz of 26% when no water had been added and 64% when 0.2% w/v of water had been added.

From the results given above it can be seen that the presence of the carbodiimide effectively stabilizes the emulsifiable concentrate against the breakdown of amitraz which occurs in the concentrate with no carbodiimide present. Examples 1 to 3 demonstrate the use of the carbodiimide at concentrations of 1 to 3% w/v.

EXAMPLE 4

An emulsifiable concentrate was prepared ny dissolving amitraz (nominally 20%), dicyclohexylcarbodiimide (3%), and a blend of calcium dodecylbenzene sulphonate and a nonylphenol ethoxylate having an ethoxy content of 14 mole per mole (10%) (sold under the trade name Agrilan B.M. by Diamond Shamrock Europe (Limited) in xylene. The solutions were tested as described in Example 1 and after three months storage at 50° C. showed no loss of amitraz.

I claim:
1. A liquid insecticidal and acaricidal composition comprising a solution of from about 0.5 to 35% w/v 1,5-di-(2,4-dimethylphenyl)-3-methyl-1,3,5-triazapenta-1,4-diene and from about 1 to 3% w/v of a carbodiimide selected from the group consisting of dicyclohexylcarbodiimide and di-(2,6-diisopropylphenyl) carbodiimide.
2. The insecticidal and acaricidal composition of claim 1 wherein the composition comprises 0.5 to 25% w/v of 1,5-di-(2,4-dimethylphenyl)-3-methyl-1,3,5-triazapenta-1,4-diene.
3. The insecticidal and acaricidal composition of claim 1 wherein the carbodiimide is dicyclohexylcarbodiimide.
4. The insecticidal and acaricidal composition of claim 1 wherein the composition is in the form of an emulsifiable concentrate.
5. The insecticidal and acaricidal composition of claim 1 wherein the carbodiimide is di-(2,6-diisopropylphenyl) carbodiimide.
6. A liquid insecticidal and acaricidal composition in the form of an emulsifiable concentrate comprising a solution of 0.5 to 25% w/v of 1,5-di-(2,4-dimethylphenyl)-3-methyl-1,3,5-triazapenta-1,4-diene and from 1 to 3% w/v of di-(2,6-diisopropylphenyl)carbodiimide.

* * * * *